(12) United States Patent
Struzinski

(10) Patent No.: US 8,932,268 B1
(45) Date of Patent: Jan. 13, 2015

(54) MEDICATION CARTRIDGE INJECTION ASSEMBLY

(71) Applicant: Edward D. Struzinski, Charlestown, RI (US)

(72) Inventor: Edward D. Struzinski, Charlestown, RI (US)

( * ) Notice: Subject to any disclaimer, the term of this patent is extended or adjusted under 35 U.S.C. 154(b) by 0 days.

(21) Appl. No.: 14/033,873

(22) Filed: Sep. 23, 2013

(51) Int. Cl.
*A61M 5/145* (2006.01)
*A61M 5/315* (2006.01)
*A61M 5/31* (2006.01)

(52) U.S. Cl.
CPC ....... *A61M 5/14566* (2013.01); *A61M 5/31568* (2013.01); *A61M 5/3137* (2013.01); *A61M 5/3157* (2013.01)
USPC .......................................... 604/218; 604/232

(58) Field of Classification Search
CPC . A61M 5/14566; A61M 5/2466; A61M 5/19; A61M 5/3137; A61M 5/31568; A61M 5/3157; A61M 5/31571; A61M 5/30; A61M 5/2459; A61M 5/286; A61M 5/288; A61M 37/0069; A61M 3/005; A61M 2005/3137; A61M 2005/3139
USPC ........... 604/27, 36, 38, 59, 60, 61, 62, 63, 64, 604/71, 72, 93.01, 181, 187, 19, 200, 201, 604/205, 218, 220, 223, 227, 228, 232–235
See application file for complete search history.

(56) References Cited

U.S. PATENT DOCUMENTS

| 3,141,583 | A | | 7/1964 | Mapel et al. |
|---|---|---|---|---|
| 4,342,310 | A | | 8/1982 | Lindmayer et al. |
| 4,447,223 | A | | 5/1984 | Kaye et al. |
| 4,531,938 | A | * | 7/1985 | Kaye et al. ...................... 604/62 |
| 4,762,515 | A | | 8/1988 | Grimm |
| 4,838,857 | A | * | 6/1989 | Strowe et al. ................... 604/67 |
| 5,569,190 | A | * | 10/1996 | D'Antonio ...................... 604/72 |
| D408,527 | S | | 4/1999 | Coelho et al. |
| D518,056 | S | | 3/2006 | Ma et al. |
| 2003/0153868 | A1 | * | 8/2003 | Azizi et al. ...................... 604/65 |
| 2008/0171996 | A1 | * | 7/2008 | Lafferty ......................... 604/187 |
| 2008/0195048 | A1 | * | 8/2008 | Niehoff .......................... 604/154 |
| 2010/0125267 | A1 | | 5/2010 | Lee et al. |

* cited by examiner

*Primary Examiner* — Nicholas Lucchesi
*Assistant Examiner* — Anh Bui

(57) ABSTRACT

A medication cartridge injection assembly facilitates and tracks dispensation of medication such as epinephrine during a heart attack. The assembly includes a frame and a housing having a plurality of chambers holding cartridges of medication. A barrel is coupled to the frame and selectively alignable with each chamber. A plunger is aligned with the barrel to engage the cartridge positioned in an aligned chamber. An actuator engages the cartridge upon manipulation of the actuator. A processor is operationally coupled to a timer actuated by manipulation of the actuator. An alert mechanism is operationally coupled to the processor to provide an alert related to a time expired since a most recent dispensing of medication.

15 Claims, 7 Drawing Sheets

MEDICATION CARTRIDGE INJECTION ASSEMBLY

BACKGROUND OF THE DISCLOSURE

Field of the Disclosure

The disclosure relates to medication injection devices and more particularly pertains to a new medication injection device for facilitating and tracking dispensation of medication given in intervals such as epinephrine during a heart attack.

SUMMARY OF THE DISCLOSURE

An embodiment of the disclosure meets the needs presented above by generally comprising a frame and a housing rotatably coupled to the frame. A plurality of chambers extend through the housing for receiving and holding a cartridge of a dose of medication. A barrel is coupled to the frame and selectively alignable with the barrel. An intravenous connection port is coupled to a distal end of the barrel relative to the frame. A plunger is coupled to the frame and aligned with the barrel wherein the plunger engages and dispenses the dose of medication from the cartridge positioned in an aligned one of the chambers through the barrel. An actuator coupled to the frame is operationally coupled to the actuator engaging the cartridge upon manipulation of the actuator. A processor coupled to the frame is operationally coupled to a timer. The timer is actuated by manipulation of the actuator. An alert mechanism is operationally coupled to the processor to provide an alert related to a time expired since a most recent dispensing of medication.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
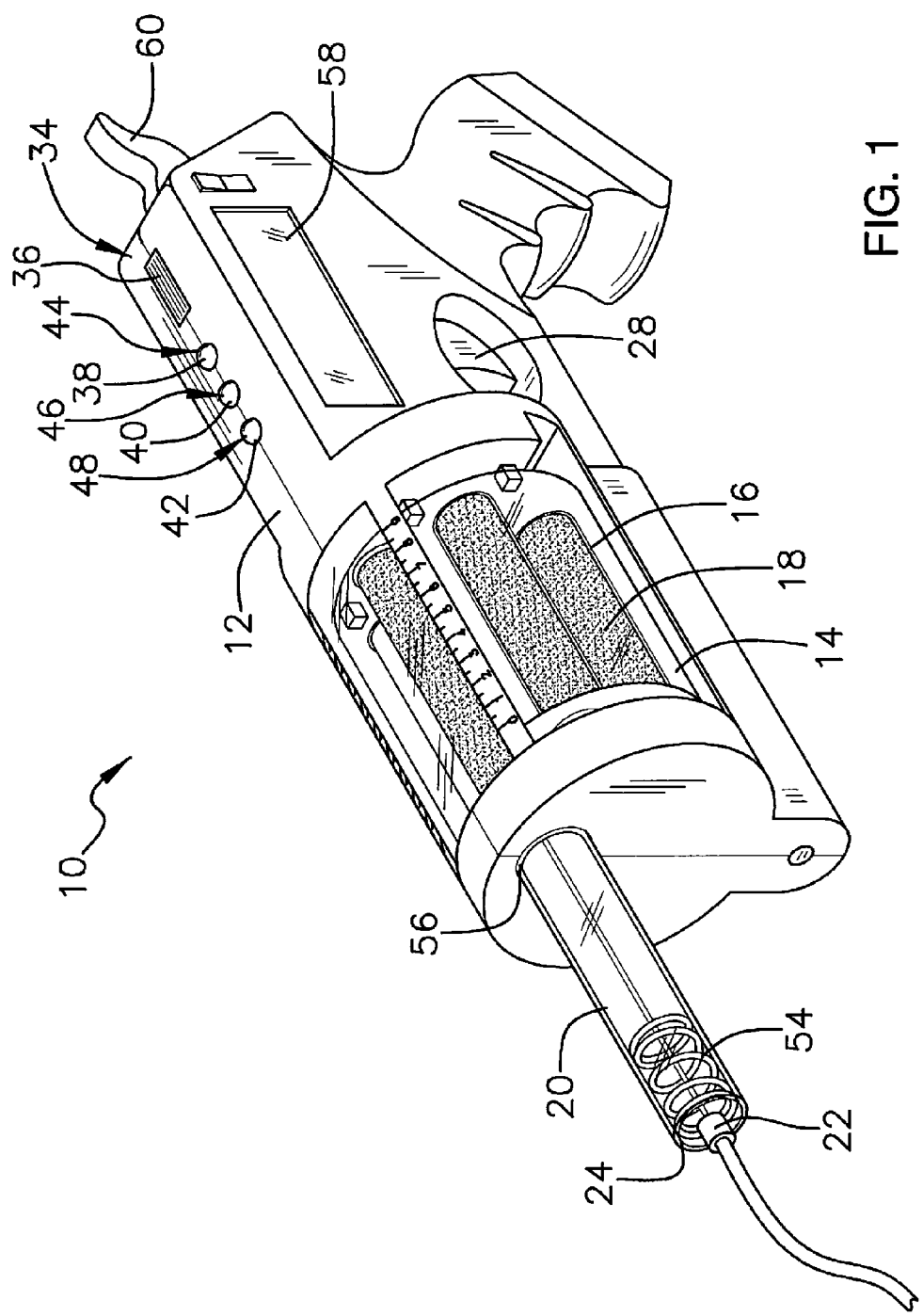
FIG. 1 is a top front side perspective view of a medication cartridge injection assembly according to an embodiment of the disclosure.
Figure 2:
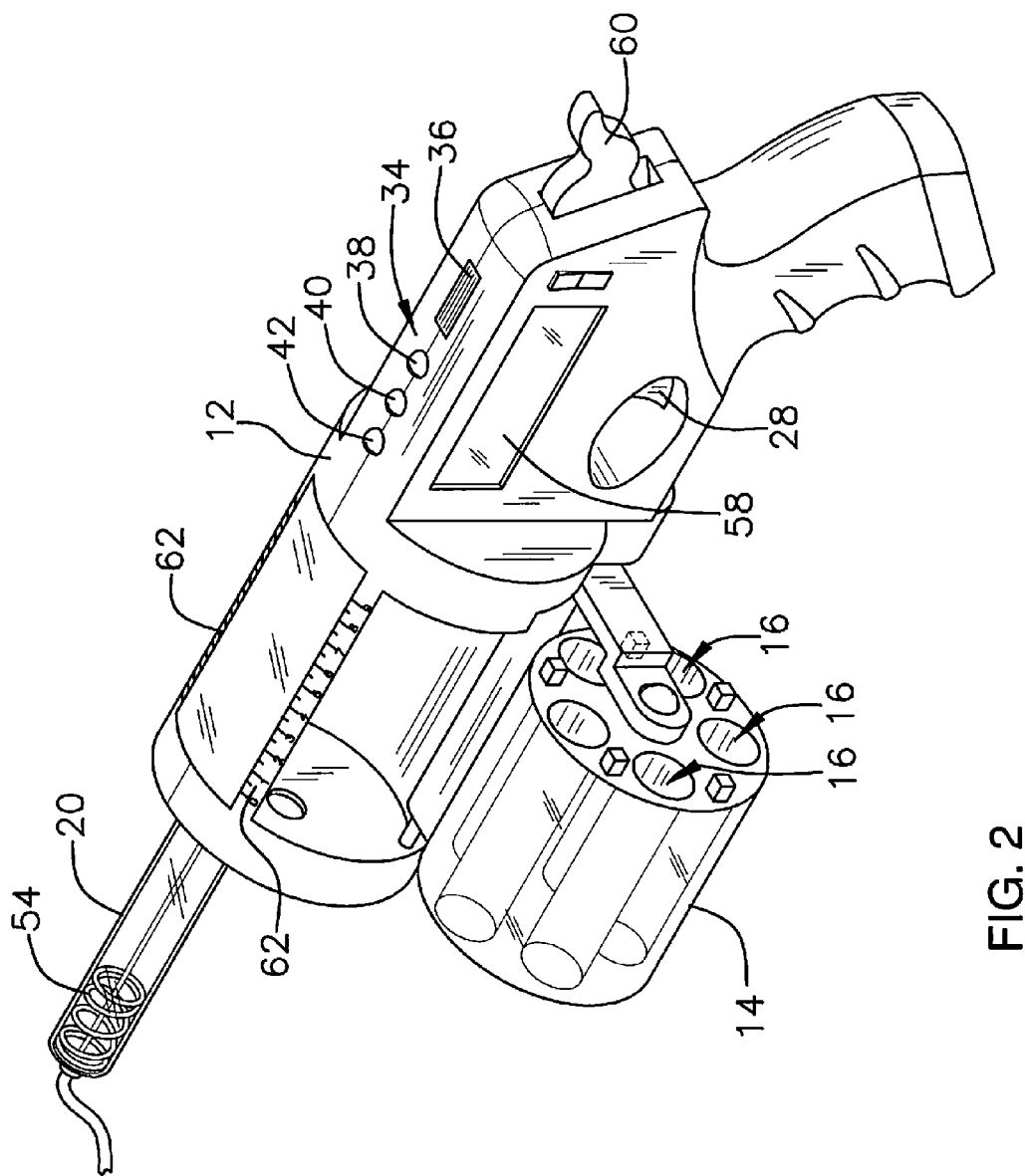
FIG. 2 is a top rear side perspective view of an embodiment of the disclosure.
Figure 3:
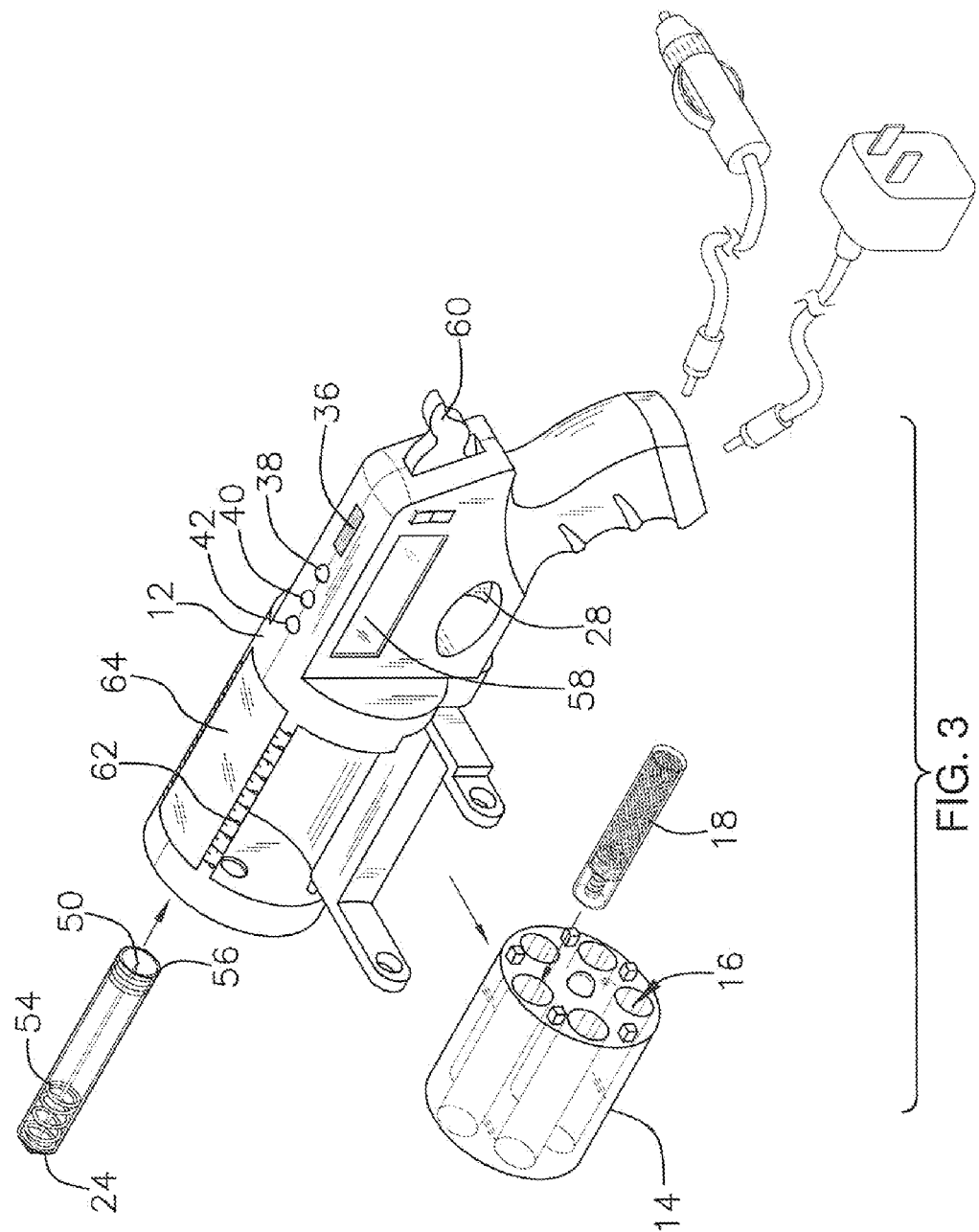
FIG. 3 is a partially exploded top rear side perspective view of an embodiment of the disclosure.
Figure 4:
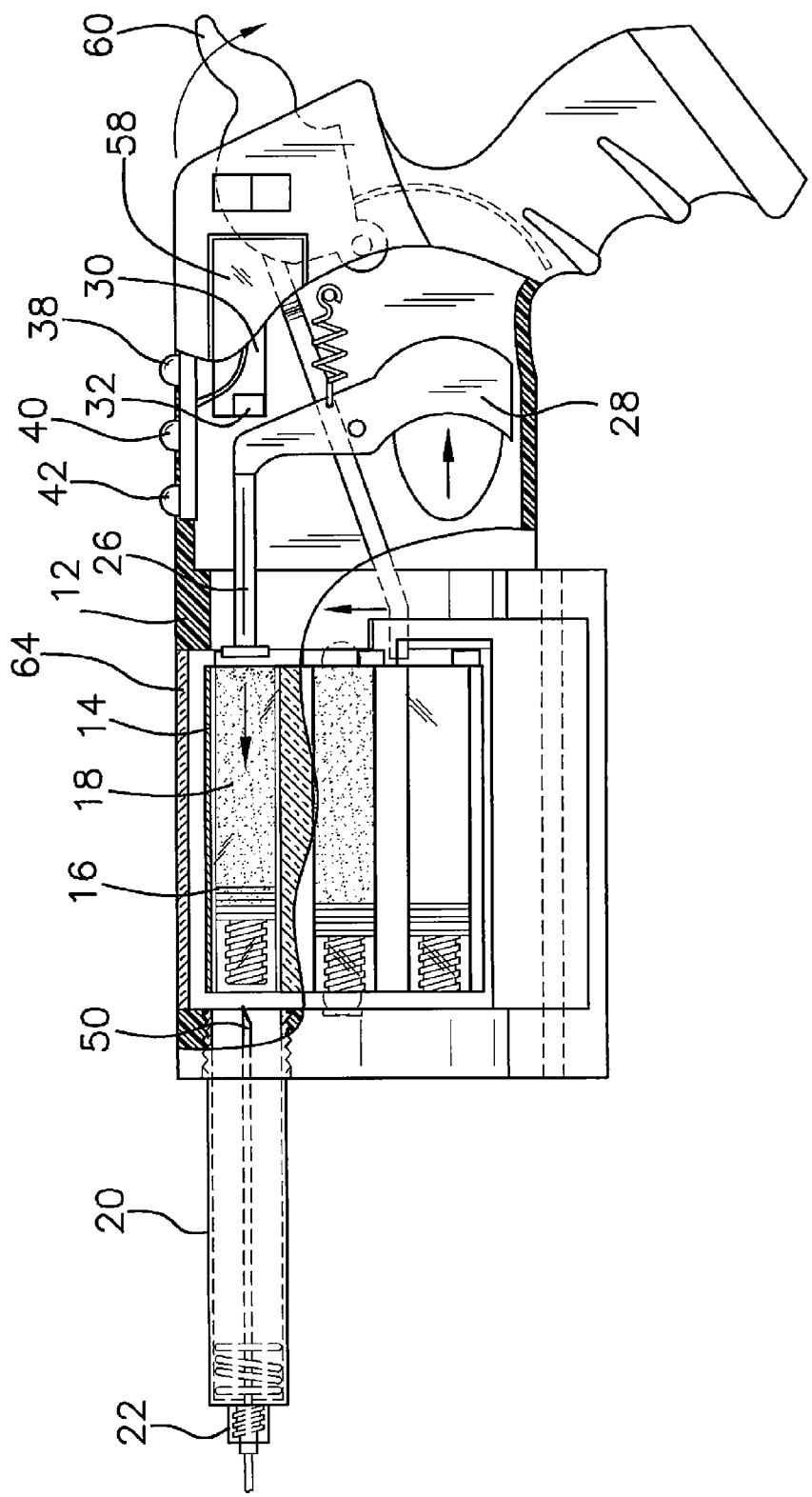
FIG. 4 is a partial cut-away side view of an embodiment of the disclosure.
Figure 5:
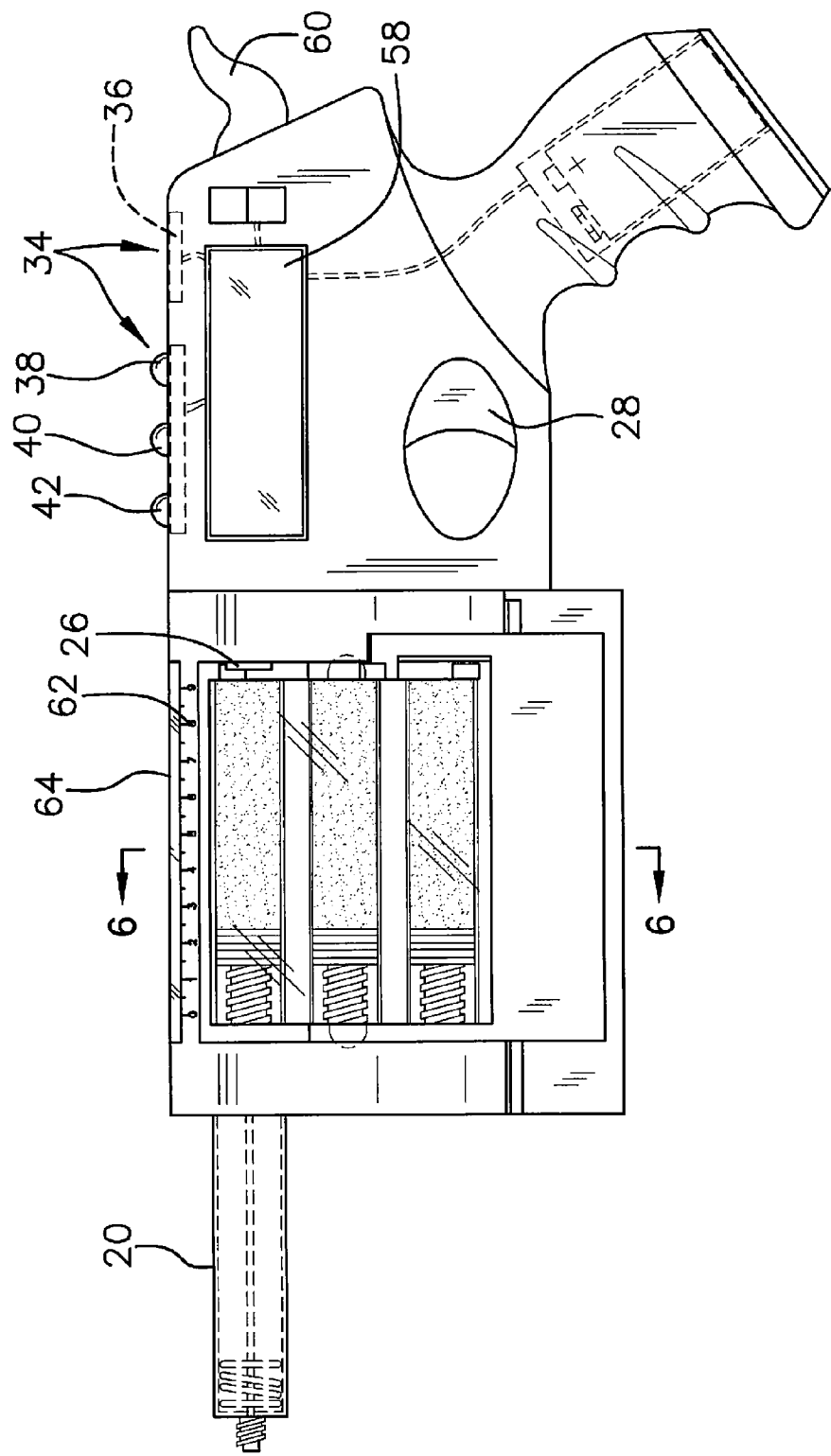
FIG. 5 is a partial cut-away side view of an embodiment of the disclosure.
Figure 6:
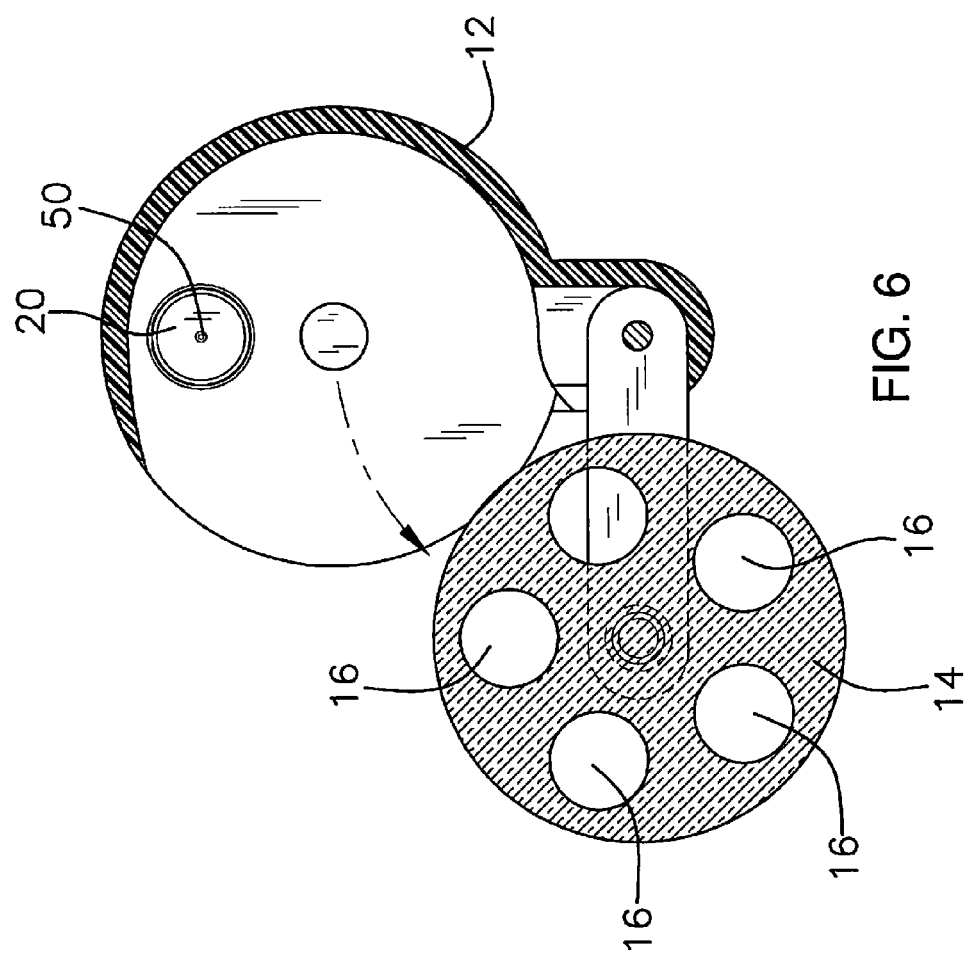
FIG. 6 is a cross-sectional view of an embodiment of the disclosure taken along line 6-6 of FIG. 5.
Figure 7:
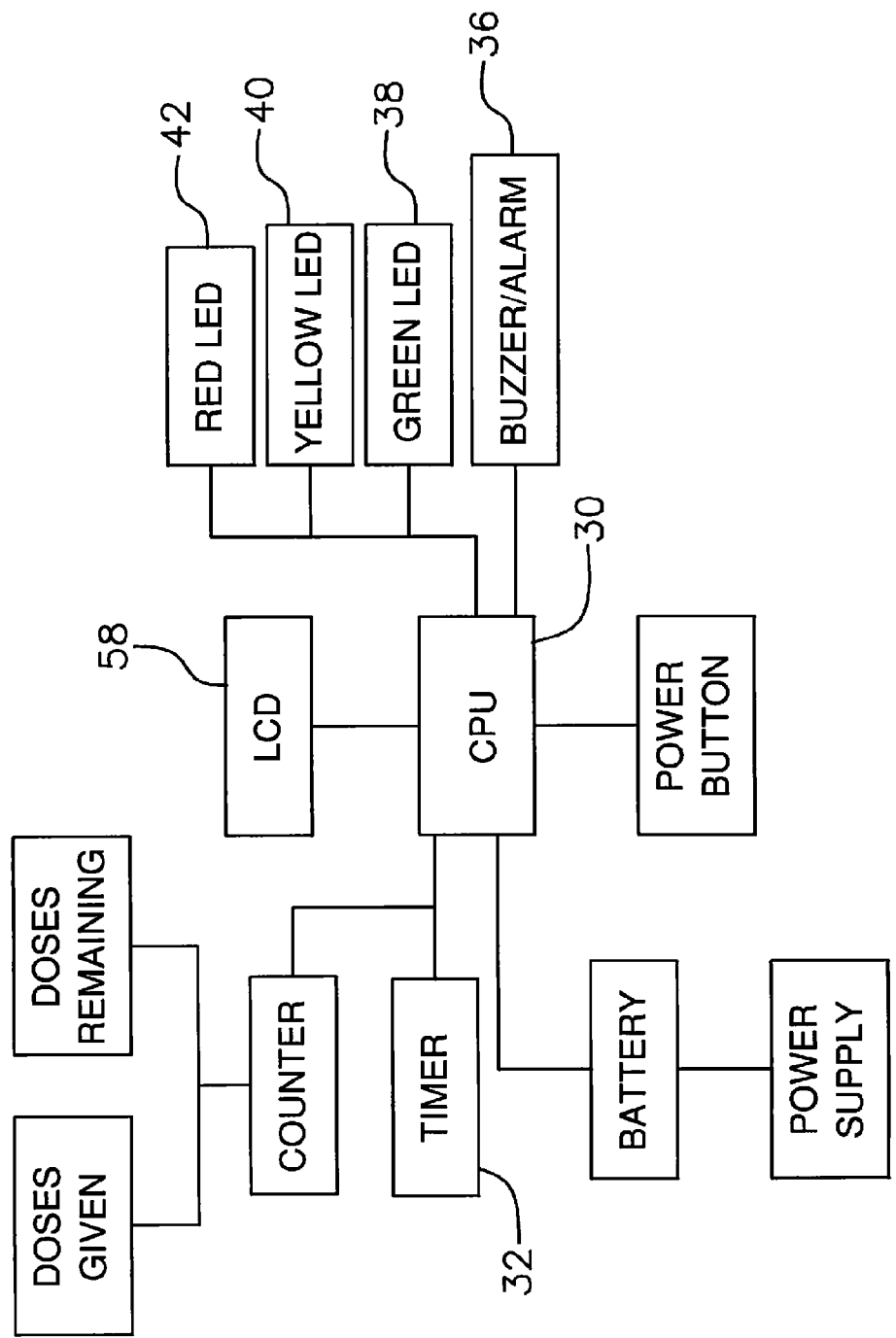
FIG. 7 is a schematic view of an embodiment of the disclosure.

With reference now to the drawings, and in particular to FIGS. 1 through 7 thereof, a new medication injection device embodying the principles and concepts of an embodiment of the disclosure and generally designated by the reference numeral 10 will be described.

As best illustrated in FIGS. 1 through 7, the medication cartridge injection assembly 10 generally comprises a frame 12 and a housing 14 rotatably coupled to the frame 12. A plurality of chambers 16 extends through the housing 14. Each chamber 16 is configured for receiving and holding a cartridge 18 of a dose of medication. A barrel 20 is coupled to the frame 12. Each chamber 16 is selectively alignable with the barrel 20. An intravenous connection port 22 is coupled to a distal end 24 of the barrel 20 relative to the frame 12. A plunger 26 is coupled to the frame 12. The plunger 26 is aligned with the barrel 20 wherein the plunger 26 is configured to engage and dispense the dose of medication from the cartridge 18 positioned in an aligned one of the chambers 16 through the barrel 20. The plunger 26 extends into the aligned chamber 16 wherein the plunger 26 urges the cartridge 18 in the aligned chamber 16 into the barrel 20. An actuator 28 is coupled to the frame 12. The plunger 26 is operationally coupled to the actuator 28 wherein the plunger 26 engages the cartridge 18 upon manipulation of the actuator 28. The housing 14 may be transparent and a transparent panel 64 may be provided adjacent to the housing 14 and aligned with the barrel 20 to permit visual inspection of the cartridge 18 aligned with the barrel 20. Indicia 62 may be positioned on opposite sides of the panel 64 indicating dosage levels so that quick inspection can confirm a desired or appropriate level of medication is being dispensed.

A processor 30 is coupled to the frame 12. A timer 32 is operationally coupled to the processor 30. The timer 32 is actuated by manipulation of the actuator 28 dispensing the dose of medication from the cartridge 18. The processor 30 may be operationally coupled to the actuator 28 in a conventional manner such that the actuator 28 is prevented from being actuated until after a selected time has expired since the most recent manipulation of the actuator 28 dispensing the dose of medication from an aligned one of the cartridges 18. An alert mechanism 34 may be coupled to the frame 12 and operationally coupled to the processor 30 wherein the alert mechanism 34 provides an alert related to a time expired since a most recent manipulation of the actuator 28 dispensing the dose of medication from the aligned cartridge 18. The alert mechanism 34 may comprise a speaker 36 operationally coupled to the processor 30. The processor 30 is programmed to selectively broadcast an audible sound from the speaker 36 relevant to the time expired since the most recent manipulation of the actuator 28 dispensing the dose of medication from the aligned cartridge 18.

The alert mechanism 34 may also comprise a first indicator light 38. The first indicator light 38 is illuminated when the actuator 28 is not being manipulated. The alert mechanism 34 may further comprise a second indicator light 40. The second indicator light 40 is illuminated immediately upon manipulation of the actuator 28 dispensing the dose of medication from the aligned cartridge 18 and remains illuminated while the actuator 28 manipulated. The alert mechanism 34 may comprise a third indicator light 42. The third indicator light 42 may be illuminated a pre-determined time after the most recent manipulation of the actuator 28 dispensing the dose of medication from the aligned cartridge 18. The pre-determined time in which the third indicator light 42 remains illuminated may be determined by a period of time needed between doses to prevent overmedication. The first indicator light 38 may be a first color 44, the second indicator light 40 may be a second color 46 distinguishable from the first color 44, and the third indicator light 42 may be a third color 48 distinguishable from the first color 44 and the second color 46.

A needle 50 is coupled to and positioned in the barrel 20 wherein the needle 50 pierces the cartridge 18 dispensing the dose of medication through the intravenous connection port 22 coupled to the barrel 20. A biasing member 54 is coupled to and positioned in the barrel 20 wherein the biasing member 54 urges the cartridge 18 back into the aligned chamber 16 when the plunger 26 is withdrawn from the aligned chamber 16. A proximal end 56 of the barrel 20 may be threadingly coupled to the frame 12 to facilitate replacement of the barrel 20.

A display 58 may be coupled to the frame 12. The display 58 is operationally coupled to the processor 30 and the timer 32 for displaying an elapsed time since the most recent manipulation of the actuator 28 dispensing the dose of medication from the aligned cartridge 18. The processor 30 is operationally coupled to the display 58 to display a number of doses administered from the housing 14. The processor 30 is operationally coupled to the display 58 to display a number of doses remaining in the housing 14. A hammer 60 may be coupled to the frame 12 wherein manipulation of the hammer 60 engages the housing 14 such that the housing 14 is rotated to align the barrel 20 from a first one of the chambers 16 into alignment with an adjacently positioned one of the chambers 16.

In use, the chambers 16 of the housing 14 are filled with the cartridges 18 holding doses of medication. The barrel 20 is attached to the intravenous connection port 22. The actuator 28 is manipulated to dispense an initial dose of the medication. The processor 30 controls the alert mechanism 34 to provide the alert to dispense medication. The processor 30 may prevent dispensing a second dose of the medication for a period of time to prevent overmedication. The housing rotates aligning a second cartridge 18 to dispense a second dose of medication when the actuator 28 is manipulated after the processor 30 will permit manipulation of the actuator 28. The first indicator light 38, second indicator light 40 and third indicator light 42 each assist in providing visual indications of the status of the assembly 10 and whether a dose of medication can or cannot be administered.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A medication cartridge injection assembly comprising:
a frame;
a housing rotatably coupled to said frame;
a plurality of chambers extending through said housing, each chamber being configured for receiving and holding a cartridge of a dose of medication;
a barrel coupled to said frame, each said chamber being selectively alignable with said barrel;
an intravenous connection port coupled to a distal end of said barrel relative to said frame;
a plunger coupled to said frame, said plunger being aligned with said barrel wherein said plunger is configured to engage and dispense the dose of medication from the cartridge positioned in an aligned one of said chambers through said barrel;
an actuator coupled to said frame, said plunger being operationally coupled to said actuator wherein said plunger engages the cartridge upon manipulation of said actuator;
a processor coupled to said frame;
a timer operationally coupled to said processor, said timer being actuated by manipulation of said actuator dispensing the dose of medication;
an alert mechanism coupled to said frame, said alert mechanism being operationally coupled to said processor wherein said alert mechanism provides an alert related to a time expired since a most recent manipulation of said actuator dispensing the dose of medication from the aligned cartridge;
said plunger extending into said aligned chamber wherein said plunger is configured to urge the cartridge in said aligned chamber into said barrel; and
a needle coupled to and positioned in said barrel wherein said needle is configured to pierce the cartridge dispensing the dose of medication through said intravenous connection port.

2. The assembly of claim 1, further comprising a biasing member coupled to and positioned in said barrel wherein said biasing member is configured to urge the cartridge back into said aligned chamber when said plunger is withdrawn from said aligned chamber.

3. The assembly of claim 1, further comprising said alert mechanism comprising a speaker operationally coupled to said processor, said processor being programmed to selectively broadcast an audible sound from said speaker relevant to the time expired since the most recent manipulation of said actuator dispensing the dose of medication from the aligned cartridge.

4. The assembly of claim 3, further comprising said alert mechanism comprising a first indicator light, said first indicator light being illuminated when said actuator is not being manipulated.

5. The assembly of claim 4, further comprising said alert mechanism comprising a second indicator light, said second indicator light being illuminated immediately upon manipulation of said actuator dispensing the dose of medication from the aligned cartridge and remaining illuminated while said actuator is being manipulated.

6. The assembly of claim 5, further comprising said alert mechanism comprising a third indicator light, said third indicator light being illuminated a pre-determined time after the most recent manipulation of said actuator dispensing the dose of medication from an aligned cartridge.

7. The assembly of claim 6, further comprising said first indicator light being a first color, said second indicator light being a second color distinguishable from said first color, and said third indicator light being a third color distinguishable from said first color and said second color.

8. The assembly of claim 1, further comprising a proximal end of said barrel being threadingly coupled to said frame.

9. The assembly of claim 1, further comprising a display coupled to said frame, said display being operationally coupled to said processor and said timer for displaying an elapsed time since the most recent manipulation of said actuator dispensing the dose of medication from an aligned cartridge.

10. The assembly of claim 9, further comprising said processor being operationally coupled to said display to display a number of doses administered from said housing.

11. The assembly of claim 9, further comprising said processor being operationally coupled to said display to display a number of doses remaining in said housing.

12. The assembly of claim 1, further comprising a hammer coupled to said frame wherein manipulation of said hammer engages said housing such that said housing is rotated to align said barrel from a first one of said chambers into alignment with an adjacently positioned one of said chambers.

13. The assembly of claim 1, further comprising said processor being operationally coupled to said actuator such that said actuator is prevented from being actuated until after a selected time expired since the most recent manipulation of said actuator dispensing the dose of medication from an aligned cartridge.

14. A medication cartridge injection assembly comprising:
a frame;
a housing rotatably coupled to said frame, said housing being transparent;
a plurality of chambers extending through said housing, each chamber being configured for receiving and holding a cartridge of a dose of medication;
a barrel coupled to said frame, each said chamber being selectively alignable with said barrel;
an intravenous connection port coupled to a distal end of said barrel relative to said frame;
a plunger coupled to said frame, said plunger being aligned with said barrel wherein said plunger is configured to engage and dispense the dose of medication from the cartridge positioned in an aligned one of said chambers through said barrel, said plunger extending into said aligned chamber wherein said plunger is configured to urge the cartridge in said aligned chamber into said barrel;
an actuator coupled to said frame, said plunger being operationally coupled to said actuator wherein said plunger engages the cartridge upon manipulation of said actuator;
a processor coupled to said frame;
a timer operationally coupled to said processor, said timer being actuated by manipulation of said actuator dispensing the dose of medication;
an alert mechanism coupled to said frame, said alert mechanism being operationally coupled to said processor wherein said alert mechanism provides an alert related to a time expired since a most recent manipulation of said actuator dispensing the dose of medication from the aligned cartridge, said alert mechanism comprising a speaker operationally coupled to said processor, said processor being programmed to selectively broadcast an audible sound from said speaker relevant to the time expired since the most recent manipulation of said actuator dispensing the dose of medication from the aligned cartridge, said alert mechanism comprising a first indicator light, said first indicator light being illuminated when said actuator is not being manipulated, said alert mechanism comprising a second indicator light, said second indicator light being illuminated immediately upon manipulation of said actuator dispensing the dose of medication from the aligned cartridge and remaining illuminated while said actuator is being manipulated, said alert mechanism comprising a third indicator light, said third indicator light being illuminated a pre-determined time after the most recent manipulation of said actuator dispensing the dose of medication from an aligned cartridge, said first indicator light being a first color, said second indicator light being a second color distinguishable from said first color, and said third indicator light being a third color distinguishable from said first color and said second color;
a needle coupled to and positioned in said barrel wherein said needle is configured to pierce the cartridge dispensing the dose of medication through an intravenous connection port;
a biasing member coupled to and positioned in said barrel wherein said biasing member is configured to urge the cartridge back into said aligned chamber when said plunger is withdrawn from said aligned chamber;
a proximal end of said barrel being threadingly coupled to said frame;
a display coupled to said frame, said display being operationally coupled to said processor and said timer for displaying an elapsed time since the most recent manipulation of said actuator dispensing the dose of medication from an aligned cartridge, said processor being operationally coupled to said display to display a number of doses administered from said housing, said processor being operationally coupled to said display to display a number of doses remaining in said housing;
a hammer coupled to said frame wherein manipulation of said hammer engages said housing such that said housing is rotated to align said barrel from a first one of said chambers into alignment with an adjacently positioned one of said chambers;
a transparent panel being coupled to said frame, said transparent panel being positioned adjacent to said housing and aligned with said barrel permitting visual inspection of said cartridge aligned with said barrel; and
indicia being positioned on opposite sides of said transparent panel indicating dosage levels.

15. The assembly of claim 14, further comprising said processor being operationally coupled to said actuator such that said actuator is prevented from being actuated until after a selected time expired since the most recent manipulation of said actuator dispensing the dose of medication from an aligned cartridge.

* * * * *